United States Patent
Aloia et al.

(10) Patent No.: US 8,881,727 B2
(45) Date of Patent: Nov. 11, 2014

(54) SYSTEM AND METHOD FOR PROVIDING FEEDBACK TO A SUBJECT REGARDING RECEPTION OF POSITIVE AIRWAY SUPPORT THERAPY

(75) Inventors: Mark Steven Aloia, Boulder, CO (US); thomas Bonnell, Export, PA (US); Erik Kurt Witt, Murrysville, PA (US); Jeffrey Lynn Kepler, Export, PA (US)

(73) Assignee: Koninklijke Philips N.V., Eindhoven (NL)

( * ) Notice: Subject to any disclaimer, the term of this patent is extended or adjusted under 35 U.S.C. 154(b) by 473 days.

(21) Appl. No.: 13/263,092

(22) PCT Filed: Mar. 15, 2010

(86) PCT No.: PCT/IB2010/051115
§ 371 (c)(1),
(2), (4) Date: Oct. 6, 2011

(87) PCT Pub. No.: WO2010/116275
PCT Pub. Date: Oct. 14, 2010

(65) Prior Publication Data
US 2012/0024287 A1 Feb. 2, 2012

Related U.S. Application Data

(60) Provisional application No. 61/167,559, filed on Apr. 8, 2009.

(51) Int. Cl.
*A61M 16/00* (2006.01)
*A62B 7/00* (2006.01)
*A62B 9/00* (2006.01)
*F16K 31/02* (2006.01)
*A61B 5/087* (2006.01)

(52) U.S. Cl.
CPC ....... *A61M 16/00* (2013.01); *A61M 2205/3584* (2013.01); *A61M 2205/3553* (2013.01); *A61M 2205/52* (2013.01); *A61B 5/087* (2013.01); *A61M 2230/46* (2013.01)
USPC ............. 128/204.23; 128/204.18; 128/205.23

(58) Field of Classification Search
USPC ............. 128/204.18, 204.21, 204.23, 202.22, 128/205.23
See application file for complete search history.

(56) References Cited

U.S. PATENT DOCUMENTS

| | | | |
|---|---|---|---|
| 6,135,106 A | 10/2000 | Dirks et al. | |
| 2004/0187871 A1 | 9/2004 | Kimmel et al. | |
| 2008/0078384 A1* | 4/2008 | Messenger et al. | 128/203.12 |

FOREIGN PATENT DOCUMENTS

| | | |
|---|---|---|
| EP | 1900387 | 3/2008 |
| WO | WO9413349 | 6/1994 |

* cited by examiner

*Primary Examiner* — Kristen Matter

(57) ABSTRACT

A system and method provide feedback to a subject regarding compliance to a positive airway pressure support therapy regime. The feedback is provided to the subject in real-time (or near real-time). The feedback indicates to the subject whether a usage goal has been achieved. The usage goal may be dynamically and adaptively determined based on past usage by the subject. This may facilitate the automatic generation of usage goals for the subject that are realistic and gradually increase the compliance of the subject over time.

15 Claims, 3 Drawing Sheets

SYSTEM AND METHOD FOR PROVIDING FEEDBACK TO A SUBJECT REGARDING RECEPTION OF POSITIVE AIRWAY SUPPORT THERAPY

CROSS-REFERENCE TO RELATED APPLICATIONS

This application claims benefit under 35 U.S.C. §119(e) of U.S. Provisional Application No. 61/167,559 filed on Apr. 8, 2009, the contents of which are herein incorporated by reference.

FIELD

The invention relates to monitoring subject usage of a system configured to deliver positive airway pressure therapy, and providing feedback to the subject that encourages extended usage of the system by the subject.

BACKGROUND

Systems for providing positive airway pressure therapy to subjects are known. These systems generate a pressurized flow of breathable gas that is provided to the airway of a subject during sleep to support the subject's airway. The support provided by the pressurized flow of breathable gas to the airway of the subject enables the subject to avoid sleep disordered breathing.

Generally, reception of a pressurized flow of breathable gas at the airway is considered uncomfortable by subjects. Conventional systems may also be inconvenient for subjects who travel and have to transport a system to in order to receive positive airway pressure therapy. Other obstacles to usage of conventional systems also exist. Consequently, compliance of subjects to positive airway pressure support regimes may be less than optimal.

SUMMARY

One aspect of the invention relates to a system configured to provide feedback to a subject regarding compliance to a positive airway pressure support therapy regime. In one embodiment, the system comprises a pressure support device, one or more sensors, and one or more processors. The pressure support device is configured to generate a pressurized flow of breathable gas for delivery to an airway of a subject. The one or more sensors are configured to generate output signals that indicate whether the pressurized flow of breathable gas is being received into the airway of the subject. The one or more processors are configured to implement computer program modules. In one embodiment, the modules comprise a usage module, a compliance module, and a feedback module. The usage module is configured to monitor usage of the pressure support device by the subject, wherein usage of the pressure support device by the subject includes receiving the pressurized flow of breathable gas into the airway. The compliance module is configured to determine whether the usage of the pressure support device by the subject has met or exceeded a predetermined usage goal. The feedback module is configured to provide feedback to the subject that indicates to the subject information related to the usage of the pressure support device with respect to the predetermined usage goal.

Another aspect of the invention relates to a method of providing feedback to a subject regarding compliance to a positive airway pressure support therapy regime. In one embodiment, the method comprises generating a pressurized flow of breathable gas for delivery to an airway of a subject; monitoring reception of the pressurized flow of breathable gas at the airway of the subject; determining therapy usage based on the reception of the pressurized flow of breathable gas at the airway of the subject; determining whether the therapy usage of the subject has met or exceeded a predetermined usage goal; and providing feedback to the subject that indicates to the subject information related to the usage of the pressure support device with respect to the predetermined usage goal.

Another aspect of the invention relates to a system configured to provide feedback to a subject regarding compliance to a positive airway pressure support therapy regime. In one embodiment, the system comprises means for generating a pressurized flow of breathable gas for delivery to an airway of a subject; means for monitoring reception of the pressurized flow of breathable gas at the airway of the subject; means for determining therapy usage based on the reception of the pressurized flow of breathable gas at the airway of the subject; means for determining whether the therapy usage of the subject has met or exceeded a predetermined usage goal; and means for providing feedback to the subject that indicates to the subject information related to the usage of the pressure support device with respect to the predetermined usage goal.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
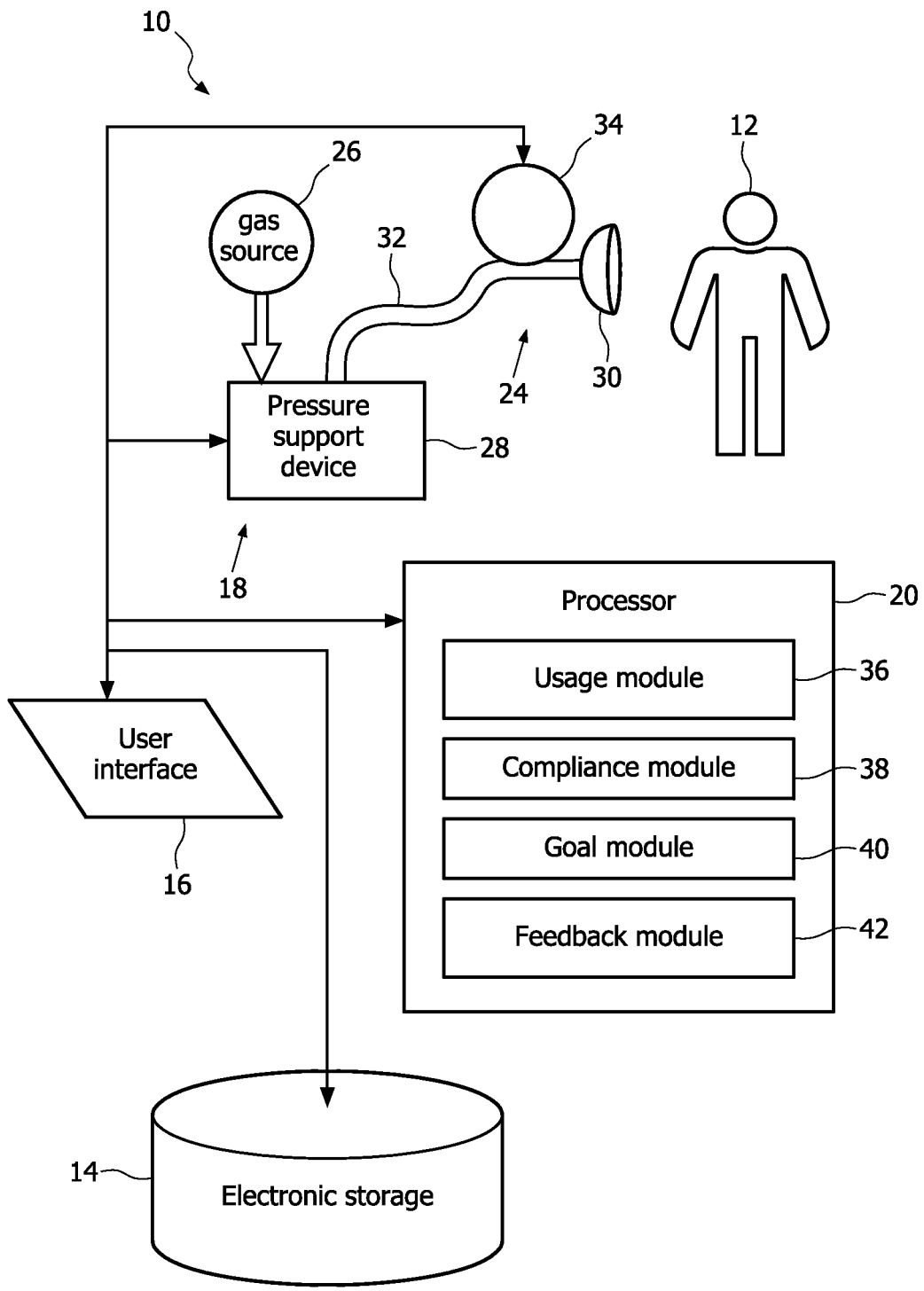
FIG. 1 illustrates a system configured to provide feedback to a subject regarding compliance to a positive airway pressure support therapy regime, in accordance with one or more embodiments of the invention.

FIG. 1 illustrates a system 10 configured to provide feedback to a subject 12 regarding compliance to a positive airway pressure support therapy regime. The feedback is provided to the subject by system 10 in real-time (or near real-time). The feedback indicates to subject 12 whether a usage goal has been achieved. The usage goal may be dynamically and adaptively determined based on past usage by subject 12. This may facilitate the automatic generation of usage goals for subject 12 that are realistic and gradually increase the compliance of subject 12 over time. In one embodiment, system 10 includes electronic storage 14, a user interface 16, a pressure generator 18, a processor 20, and/or other components.

In one embodiment, electronic storage 14 comprises electronic storage media that electronically stores information. The electronically storage media of electronic storage 14 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 14 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 14 may store software algorithms, computer program modules, information determined by processor 20, information received via user interface 16, and/or other information that enables system 10 to function properly. Electronic storage 14 may be a separate component within system 10, or electronic storage 14 may be provided integrally with one or more other components of system 10. Although electronic storage 14 is illustrated in FIG. 1 as a single entity, in one embodiment, electronic storage 14 includes a plurality of electronic media divided amongst a plurality of different devices and/or components within system 10.

User interface 16 is configured to provide an interface between system 10 and subject 12. The interface between system 10 and subject 12 enables the subject 12 to provide information to and receive information from system 10. This enables data, results, feedback, and/or instructions and any other communicable items, collectively referred to as "information," to be communicated between subject 12 and system 10. Examples of interface devices suitable for inclusion in user interface 16 include a keypad, buttons, switches, a keyboard, knobs, levers, a display screen, a touch screen, speakers, a microphone, an indicator light, an audible alarm, and/or a printer. User interface 16 may include one or more graphical user interfaces provided to users via electronic processing platforms (e.g., a desktop computer, a laptop computer, a handheld computer, a mobile communication device, etc.). The graphical user interface provided to users may be accessible via a web-based information portal.

It is to be understood that other communication techniques, either hard-wired or wireless, are also contemplated by the present invention as user interface 16. For example, the present invention contemplates that user interface 16 may be integrated with a removable storage interface provided by electronic storage 14. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 16 include, but are not limited to, an RS-232 port, RF link, an IR link, modem (telephone, cable or other). In short, any technique for communicating information with system 10 is contemplated by the present invention as user interface 16.

Pressure generator 18 is configured to generate a pressurized flow of breathable gas for delivery to the airway of subject 12 by a circuit 24. One or more parameters of the pressurized flow of breathable gas generated by pressure generator 18 may be controlled in accordance with a pressure therapy algorithm designed to provide positive airway pressure support to subject 12 during bedtime. The pressure therapy algorithm may include one or more of a bi-PAP algorithm, a CPAP algorithm, auto-titrating CPAP, servo-ventilation, backup breaths, comfort features such as C-Flex, reducing pressure during early exhalation, and/or other pressure therapy algorithms. The one or more parameters of the pressurized flow of breathable gas controlled in accordance with the pressure therapy algorithm may include one or more of a pressure, a flow rate, a composition, a volume, and/or other parameters of the pressurized flow of breathable gas. In one embodiment, pressure generator 18 includes a gas source 26 and a pressure support device 28.

Gas source 26 includes a body or bodies of gas from which pressure support device 28 generates the pressurized flow of breathable gas that is delivered to subject 12. Gas source 26 may include any supply of breathing gas, such as, for example, ambient atmosphere, a tank of pressurized gas, a wall gas source, and/or other bodies of breathable gas. The breathing gas from gas source 26 can be any breathable gas, such as air, oxygen, an oxygen mixture, a mixture of a breathing gas and a medication, which can be in gaseous form (e.g., nitric oxide, nebulized, etc.), and/or other breathable gases.

Pressure support device 28 includes one or more mechanisms for controlling one or more parameters of the flow of breathable gas released from pressure support device 28 to circuit 24 (e.g., pressure, flow, etc.). For example, pressure support device 28 may include one or more of a valve, a blower, a piston, a bellows, and/or other mechanisms for controlling one or more parameters of the flow of breathable gas.

Circuit 24 defines a gas flow path between pressure generator 18 and the airway of subject 12. As such, circuit 24 is configured to deliver the pressurized flow of gas from pressure generator 18 to the airway of subject 12. In one embodiment, circuit 24 includes one or more of an interface appliance 30 and a conduit 32.

Interface appliance 30 is configured to provide gas to and receive gas from the airway of subject 12. Interface appliance 30 may include may include either an invasive or non-invasive appliance for communicating gas between circuit 24 and the airway of subject 12. For example, interface appliance 30 may include a nasal mask, nasal/oral mask, total face mask, nasal cannula, endotracheal tube, LMA, tracheal tube, and/or other interface appliance.

Conduit 32 forms a flow path between pressure support device 18 and interface appliance 30. In one embodiment, conduit 32 is flexible.

Although circuit 24 is illustrated in FIG. 1 as a single-limbed circuit for communicating a pressurized flow of breathable gas with the airway of subject 12, this is not intended to be limiting. In one embodiment circuit 24 is a double-limbed circuit with a separate portion configured to convey gas away from the airway of subject 12.

In one embodiment, system 10 includes one or more sensors 34. The sensors 34 are configured to monitor one or more parameters of the pressurized flow of breathable gas delivered to the airway of subject 12. For example, sensors 34 may include one or more sensors configured to generate output signals conveying information related to one or more a pressure, a flow rate, a composition, a volume, and/or other parameters of the pressurized flow of breathable gas. Such sensors may include, for instance, one or more of a pressure sensor, a flowmeter, a capnometer, and/or other sensors configured to generate output signals conveying information related to one or more parameters of the pressurized flow of breathable gas. The sensors 34 may be disposed in system 10 so as to be in communication with the pressurized flow of breathable gas inside pressure support device 28, inside circuit 24, and/or at or near the airway of subject 12. For example, one or more of sensors 34 may be disposed in a positive airway pressure support system that includes pressure support device 28, interface appliance 30, and/or conduit 32.

In one embodiment, some or all of the structure and function attributed to electronic storage 14 and/or user interface 16 may be incorporated into system 10 with pressure support device 28 in a positive airway pressure support system. In this embodiment, the positive airway pressure support system includes a user interface that enables subject 12 to provide information to and/or receive information from the positive airway pressure support system. This user interface provides at least some of the structure and function attributed to user interface 16. The positive airway pressure support system includes one or more electronic storage media that store, for instance, algorithms, modules, and/or data associated with the therapy provided to subject 12. These same one or more electronic storage media may provide at least some of the structure and function attributed to electronic storage 14. Similarly, some or all of the structure and function attributed to processor 20 below may be provided by one or more processors disposed within the positive airway pressure support system that includes pressure support device 28.

Processor 20 is configured to provide information processing capabilities in system 10. As such, processor 20 may include one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 includes a plurality of processing units.

As is shown in FIG. 1, in one embodiment, processor 22 is configured to execute one or more computer program modules to provide the functionality attributed to processor 22 herein. The one or more computer program modules may include one or more of a usage module 36, a compliance module 38, a goal module 40, a feedback module 42, and/or other modules. Modules 36, 38, 40, and/or 42 may be implemented in software; hardware; firmware; some combination of software, hardware, and/or firmware; and/or otherwise implemented. It should be appreciated that although modules 36, 38, 40, and/or 42 are illustrated in FIG. 1 as being co-located within a single processing unit, in implementations in which processor 20 includes multiple processing units, one or more of modules 36, 38, 40, and/or 42 may be located remotely from the other modules. Further, the description of the functionality provided by the different modules 36, 38, 40, and/or 42 set forth below is for illustrative purposes, and is not intended to be limiting. Any of modules 36, 38, 40, and/or 42 may provide more or less functionality than is described. For example, one or more of modules 36, 38, 40, and/or 42 may be eliminated, and some or all of its functionality may be provided by other ones of modules 36, 38, 40, and/or 42. As another example, processor 20 may execute one or more additional modules that may perform some or all of the functionality attributed below to one of modules 36, 38, 40, and/or 42.

The usage module 36 is configured to monitor usage of pressure generator 18 by subject 12. As will be appreciated, the therapeutic benefits of the pressurized flow of breathable gas provided to subject 12 by pressure generator 18 may be enhanced as subject 12 increases the amount of time for which the pressurized flow of breathable gas is received by subject 12. However, subject 12 may find using pressure generator 18 inconvenient, uncomfortable, and/or otherwise troublesome. In monitoring usage of pressure generator 18 by 12, usage module 36 quantifies the amount of therapy received by subject 12 from pressure generator 18. For example, the usage of pressure generator 18 by subject 12 may be quantified as the amount of time for which subject 12 receives the pressurized flow of breathable gas from pressure generator 18 via interface appliance 30. Other quantifications of the therapy received by subject 12 from pressure generator 18 may be implemented without departing from the scope of this disclosure.

Usage module 36 monitors usage of pressure generator 18 based on the output signals generated by sensors 34. For example, from the output signals generated by sensors 34, usage module 36 may determined whether or not subject 12 is receiving the pressurized flow of breathable gas from pressure generator 18 at a given time. This includes determining whether interface appliance 30 is installed properly at the airway of subject 12 and determining whether the pressurized flow of breathable gas is currently being generated by pressure generator 18. From this determination, usage module 36 quantifies usage of pressure generator 18 by subject 12 (e.g., by aggregating the time during which subject 12 received the pressurized flow of breathable gas), which provides a measurement of the amount of therapy received by subject 12.

In monitoring usage of pressure generator 18, usage module 36 may quantify usage of pressure generator 18 during individual epoch periods of time and/or during era periods of time that span a plurality of epochs. By way of non-limiting example, epochs may be individual days/nights (e.g., 24 hour periods), and eras may be a predetermined number of days (e.g., a week, 10 days, a month, etc.).

Figure 2:
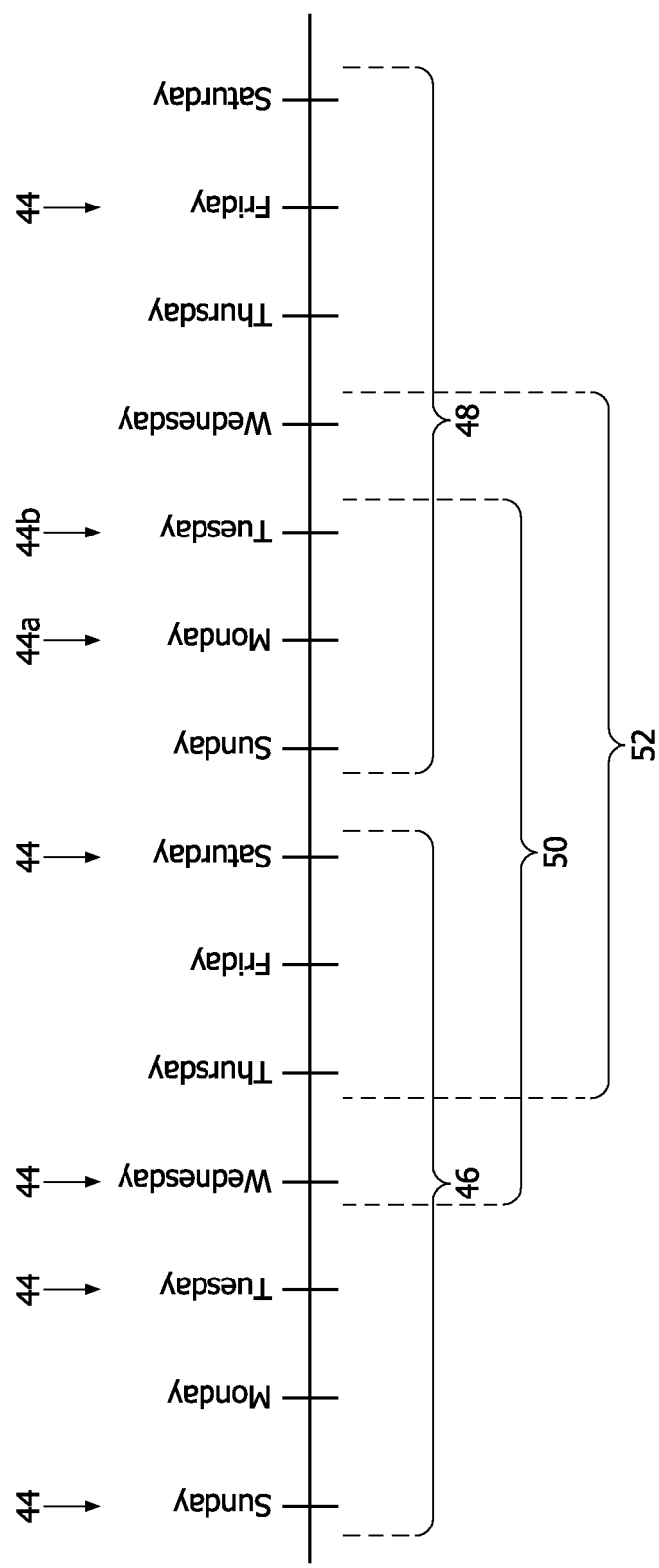
FIG. 2 is a timeline that illustrates the manner in which compliance to a therapy regime is monitored, according to one or more embodiments of the invention.

By way of illustration, FIG. 2 depicts the manner in which a module, such as usage module 36 (shown in FIG. 1), monitors usage of a pressure generator by a subject to receive therapy in the form of a pressurized flow of breathable gas delivered to the airway of the user from the pressure generator, according to one embodiment. FIG. 2 includes a timeline that is divided into a plurality of epochs 44. In particular, epochs 44 are individual nights. In the embodiment illustrated in FIG. 2, usage is quantified by the module in terms of the amount of time during a given epoch for which the subject has received the pressurized flow of breathable gas to the airway.

In addition to quantifying usage on a per epoch basis, the module also quantifies usage on a per era basis. In the exemplary embodiment illustrated in FIG. 2, an era is a week (e.g., 7 nights). However, this number of epochs is not intended to be limiting. The module quantifies usage received for a given era by aggregating the usage by the subject during the epochs within the given era. This aggregation may include, for example, adding the amounts of usage, averaging the amounts of usage, determination based on mode, determination of median or mean, discarding outliers (e.g., highest, lowest) prior to aggregating, weighting contributions (e.g., previous day is weighted heaviest while oldest day is weighted least), and/or otherwise aggregating the amounts of usage.

The eras defined by the module may include fixed, non-overlapping periods of time, or an era may be a rolling window of time having a predetermined length. By way of example, FIG. 2 illustrates two consecutive eras 46 and 48 that are fixed in time. Eras 46 and 48 are weeklong periods that span the traditional week (Sunday-Saturday). FIG. 2 further illustrates eras 50 and 52, which would be defined as eras by the module were using a rolling window of time as eras. At the Monday illustrated in FIG. 2 as 44a, the current era would be defined by the module as era 50. On the following day, Tuesday 44b, the current era is defined by the module as era 52, and so on.

Returning to FIG. 1, compliance module 38 is configured to monitor compliance of subject 12 in the usage of pressure generator 18. Monitoring compliance of subject 12, in one embodiment, includes determining whether the usage of pressure generator 18 by subject 12 has met or exceeded a predetermined usage goal. Determinations by compliance module 38 of compliance may be made on an epoch and/or era basis. To monitor compliance on an epoch basis, compliance module 38 compares usage during a given epoch with a predetermined usage goal for the determined epoch. To monitor compliance on an era basis, compliance module 38 compares usage during a given era with a predetermined era goal.

Determinations of compliance may be made by compliance module 38 for time periods (e.g., epochs, eras, etc.) that have passed and/or for time periods that are currently occurring. For example, in the middle of a given epoch, compliance module 38 determines compliance of subject 12 for the given epoch by comparing the current amount of usage by subject 12 with a predetermined usage goal for the given epoch. The predetermined usage goal may be prorated based on the current time within the given epoch, or current usage may be compared against the full usage goal even though the given epoch has not yet been concluded.

Goal module 40 is configured to determine usage goals for implementation by compliance module 38. As is discussed further below, the goal module 40 determines usage goals dynamically and adaptively to encourage compliance by subject 12. In one embodiment, the usage goals are determined by goal module 40 based on past usage of pressure generator 18 by subject 12. The goals determined by goal module 40 may include epoch usage goals and/or era usage goals. In addition to determining the usage goals, goal module 40 may provide the usage goals to subject 12 in advance so that subject 12 knows what upcoming goals are and/or adjust upcoming goals. The goal module 40 may provide the usage goals to subject 12, and/or receive adjustments to the goals from subject 12, via user interface 16.

Feedback module 42 is configured to provide feedback to subject 12 that indicates to subject 12 whether or not subject 12 has met or exceeded usage goals. The feedback may explicitly indicate whether subject 12 has met or exceeded usage goals. This feedback is determined based on the determinations of compliance made by compliance module 38. The feedback provided to subject 12 by feedback module 42 may include one or more of visual feedback, audio feedback, tactile feedback, and/or other feedback. To provide the feedback to subject 12, in one embodiment, feedback module 42 generates feedback that is delivered to subject 12 via user interface 16.

In one embodiment, the feedback provided by feedback module 42 includes more than a simple indication of whether subject 12 has met one or more usage goals. In this embodiment, feedback module 42 further provides feedback to subject 12 that is intended to motivate subject 12. By way of non-limiting example, the feedback may include messages that indicate benefits of positive airway pressure therapy provided by system 10, messages that convey empathy about the inconvenience, discomfort, or other issues that discourage compliance if subject 12 does not meet the usage goal(s), messages that indicate completion of an epoch goal that provide encouragement to proceed with completion of the overarching era goal, and/or other messages.

In one embodiment, feedback module 42 is further configured to provide feedback to a caregiver. The feedback provided to the caregiver indicates to the caregiver whether subject 12 has met or exceeded one or more usage goals. Feedback module 42 may be configured to provide this feedback in real-time or near real-time, or may be configured to store the feedback and provide feedback corresponding to some length of time to the caregiver at a later date. By way of non-limiting example, feedback module 42 may provide feedback to the caregiver via removable storage media, over a network connection (e.g., via electronic message, web portal, voice mail, or other communication media), by a wireless transmission (e.g., text message or other wireless communication media), or via other communication media).

Figure 3:
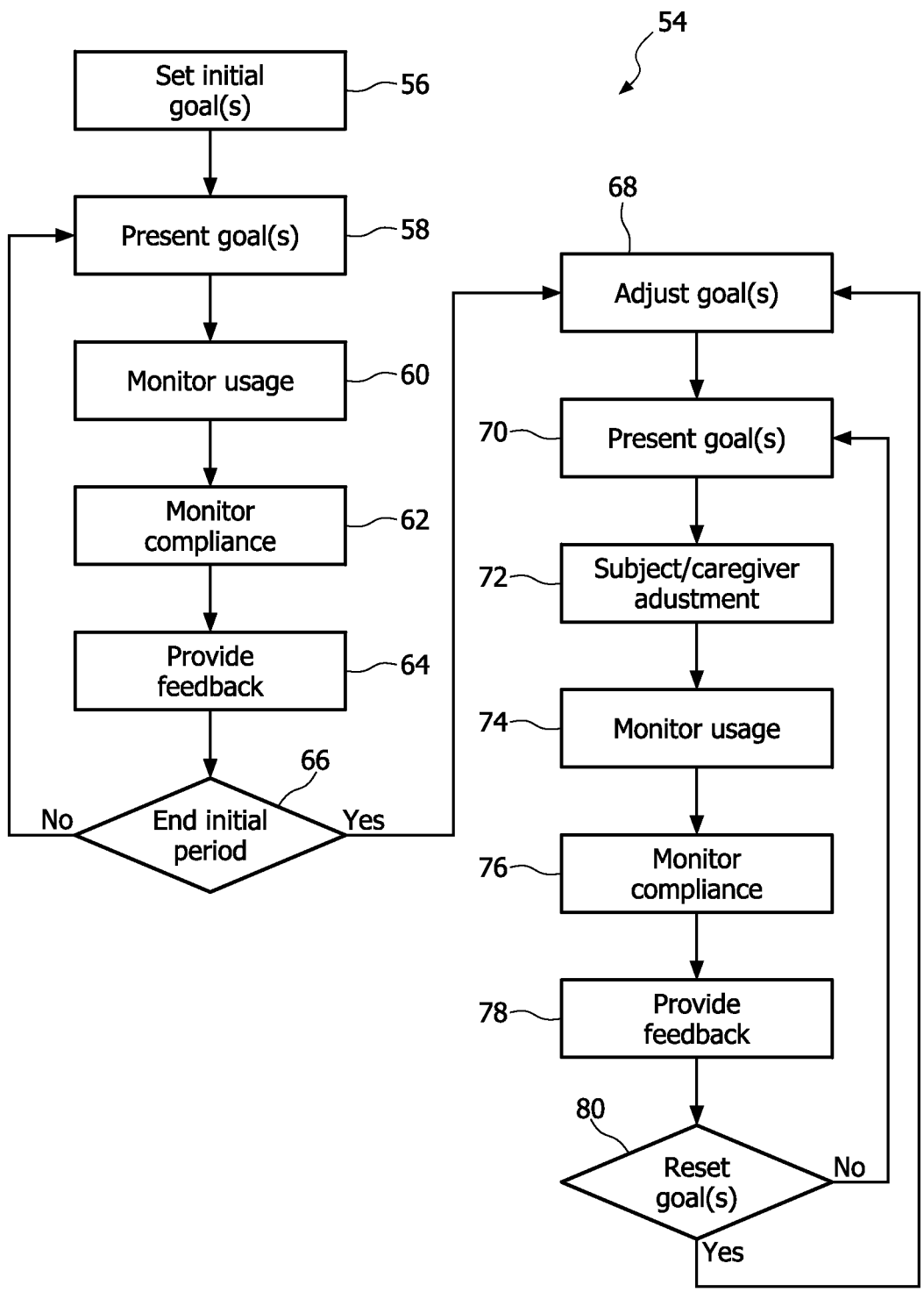
FIG. 3 illustrates a method of monitoring compliance of a subject with positive airway pressure treatment, and/or of providing feedback to the subject to encourage compliance, in accordance with one or more embodiments of the invention.

FIG. 3 illustrates a method 54 of monitoring compliance of a subject with positive airway pressure treatment, and/or of providing feedback to the subject to encourage compliance. Reception of the positive airway pressure treatment by the subject includes receiving a pressurized flow of breathable gas generated by a pressure support device. During therapy, the pressurized flow of breathable gas is received in airway of the subject to support the airway of the subject during bedtime (e.g., to avoid sleep disordered breathing). The operations of method 54 presented below are intended to be illustrative. In some embodiments, method 54 may be accomplished with one or more additional operations not described, and/or without one or more of the operations discussed. Additionally, the order in which the operations of method 54 are illustrated in FIG. 3 and are described below is not intended to be limiting. In some embodiments, method 54 may be implemented in a system that is the same as or similar to system 10 (shown in FIG. 1). However, in some embodiments, the method 54 may be implemented in other contexts without departing from the scope of this disclosure.

At an operation 56, one or more initial usage goals are determined. In one embodiment, the one or more initial usage goals include an era goal and/or an epoch goal. The initial usage goals identify a goal amount of positive airway pressure therapy that the subject should receive during a corresponding epoch and/or era. The epoch goal corresponds to one or more epochs (e.g., to individual nights). The era goal corresponds to an overarching time period that includes a plurality of epochs (e.g., a week). The epoch goals for the individual epochs within the era may be determined by dividing the era goal by the number of epochs in the era, or the epoch goals may be different from each other. The initial usage goals may be determined based on preset system settings, caregiver input, input from the subject, and/or other parameters. In one embodiment, the one or more initial usage goals are determined by a goal module that is the same as or similar to goal module 40 (shown in FIG. 1 and described above).

At an operation 58, at least one of the one or more initial goals are presented to the subject. The goal(s) presented to the subject include a current epoch goal corresponding to the current or upcoming epoch, and/or a current era goal corresponding to the current or upcoming era. In one embodiment, operation 58 is performed by a goal module and user interface that are similar to or the same as goal module 40 and user interface 16 (shown in FIG. 1 and described above).

At an operation 60, usage by the subject is monitored for a current epoch and/or a current era. This may include determining an amount of time for which the subject receives the pressurized flow of breathable gas to his airway during the current epoch and/or the current era. In one embodiment, operation 60 is performed by a usage module that is the same as or similar to usage module 36.

At an operation 62, compliance of the subject is monitored. Monitoring the compliance of the subject with the positive airway pressure therapy includes comparing the initial epoch and/or era goals determined at operation 56 with the usage monitored at operation 60 to determine whether the user has met or exceeded the initial epoch and/or era goals. In one embodiment, operation 62 is performed by a compliance module that is the same as or similar to compliance module 38.

At an operation 64, feedback is provided to the subject that indicates the compliance monitored at operation 62. This feedback indicates to the subject whether the subject has received enough positive airway pressure therapy to satisfy the initial epoch and/or initial era goals. In one embodiment, operation 64 further includes providing feedback to a caregiver associated with the subject. The feedback provided to the caregiver indicates whether the subject has satisfied the initial epoch and/or initial era goals. In one embodiment, operation 64 is performed by a feedback module that is the same as or similar to feedback module 42 (shown in FIG. 1 and described above).

At an operation 66, a determination is made as to whether an initial period of time during which the initial usage goal(s) determined at operation 56 are used has expired. The initial period of time may include a fixed period of time (e.g., a predetermined number of epochs and/or eras), or the initial period of time may be a dynamic period of time that enables a clear pattern of usage by the subject to be determined. If the initial period of time is dynamic, then operation 66 includes determining whether a clear pattern of usage can be determined. If the initial period of time is static, then the amount of time that the initial usage goals have been used to monitor compliance is compared with the static period of time. In one embodiment, operation 66 is performed by a processor that is the same as or similar to processor 20 (shown in FIG. 1 and described above). The determination made at operation 66 may be made by the processor in an entirely automated manner, or may be subject to outside inputs (e.g., from the caregiver and/or the subject).

If it is determined at operation 66 that the initial period time has not expired, then method 54 returns back to 58. If it is determined at operation 66 that the initial period of time has expired, then method 54 proceeds to an operation 68. At operation 68, one or more new usage goal(s) are determined. The determination of new usage goal(s) at operation 68 may be dynamic and adaptive based on previous usage by the subject. The determination of usage goal(s) dynamically at operation 68 is designed to provide the subject with realistic usage goals that continually coax the subject toward enhanced usage. By way of non-limiting example, at operation 66 the new usage goal(s) may include a new epoch goal and new era goal. The new epoch goal may be an increase of some amount over per epoch usage of the subject during the initial period of time. Similarly, the new era goal may be an increase of some amount over per era usage during the initial period of time. For instance, per epoch and/or per era usage during the initial period of time may be increased by about 10%, about 20%, about 30%, some amount between about 10% and about 30%, and/or by some other predetermined amount. It will be appreciated that techniques other than a percent increase may be implemented without departing from the scope of this disclosure. In one embodiment, operation 68 is performed by a goal module that is the same as or similar to goal module 40 (shown in FIG. 1 and described above).

In one embodiment, method 54 does not include an initial period. In this embodiment, method 54 begins at operation 68 and usage goals are determined based on caregiver settings, based on predetermined, generic goals, or otherwise determined without taking into account past usage by the subject.

At an operation 70, at least one of the one or more usage goals determined at operation 68 are presented to the subject. The usage goal(s) presented to the subject include a current epoch goal corresponding to the current or upcoming epoch, and/or a current era goal corresponding to the current or upcoming era. In one embodiment, operation 70 is performed by a goal module and user interface that are similar to or the same as goal module 40 and user interface 16 (shown in FIG. 1 and described above).

At an operation 72, the one or more current usage goals may be adjusted at the discretion of the subject and/or the caregiver. Enabling the subject to adjust the usage goals provides the subject with some degree of control over treatment regime. For example, the subject may feel that an epoch and/or era goal is not large enough, and the he is capable of greater usage. To challenge himself, the subject may increase the usage goal. As another example, the subject may feel than an epoch and/or era goal is too large. The subject may decrease the usage goal(s) to set the standard against which usage is measured at a more attainable level. In some instances, the subject may adjust usage goals to coincide with scheduling. For example, if the subject knows that he will only be able to get 5 hours of rest in a given night, an epoch usage goal for the given night of 6 hours would not be realistic. Operation 72 enables the subject to decrease the epoch usage goal to an amount of time that fits within the parameters of the subject's schedule. The amount by which the subject can adjust goals may be bounded by a fixed period of time (e.g., goal can be no less than 3 hours), by a fixed amount (e.g., 2 hours, 3 hours, etc.), or by an amount that is relative to the goal (e.g., 10% of the goal, 20% of the goal, etc.). In one embodiment, an upper bound on adjustments that can be made by the subject is governed by a rule that is different than a lower bound on adjustments that can be made by the subject.

Enabling the caregiver to adjust the usage goals determined at operation 68 facilitates caregiver control over the treatment of the subject. The caregiver may increase or decrease the usage goals in accordance with the needs and/or abilities of the subject. In one embodiment, enabling the caregiver to adjust the usage goals at operation 72 includes enabling the caregiver to set the amount(s) by which the subject can adjust the usage goals. For example, the caregiver may specify a percent change or fixed amount beyond which the subject cannot adjust usage goals.

In one embodiment, adjustments to one usage goal by the subject and/or the caregiver cause corresponding adjustments to other related usage goals. These adjustments to related usage goals may be transparent to the subject and/or the caregiver. For instance, an adjustment to an epoch goal corresponding to a giver epoch by the subject or caregiver may result in an adjustment to an era goal corresponding to an era that includes the given epoch.

In one embodiment, operation 72 is performed by a goal module and a user interface. The goal module and the user interface may be the same as or similar to goal module 40 and user interface 16.

At an operation 74, usage by the subject is monitored for a current epoch and/or a current era. This may include determining an amount of time for which the subject receives the pressurized flow of breathable gas to his airway during the current epoch and/or the current era. In one embodiment, operation 74 is performed by a usage module that is the same as or similar to usage module 36.

At an operation 76, compliance of the subject is monitored. Monitoring the compliance of the subject with the positive airway pressure therapy includes comparing the epoch and/or era goals determined at operation 68 and/or adjusted at operation 72 with the usage monitored at operation 74 to determine whether the user has met or exceeded the epoch and/or era goals. In one embodiment, operation 76 is performed by a compliance module that is the same as or similar to compliance module 38.

At an operation 78, feedback is provided to the subject that indicates the compliance monitored at operation 76. This feedback indicates to the subject whether the subject has received enough positive airway pressure therapy to satisfy the epoch and/or era goals (or other usage goals) determined at operation 68. In one embodiment, operation 78 further includes providing feedback to a caregiver associated with the subject. The feedback provided to the caregiver indicates whether the subject has satisfied the epoch and/or era goals (or other usage goals) determined at operation 68. In one embodiment, operation 78 is performed by a feedback module that is the same as or similar to feedback module 42 (shown in FIG. 1 and described above).

At an operation 80, a determination is made as to whether one or more usage goals need to be adjusted. Usage goals may be set for adjustment at predetermined intervals. By way of example, in one embodiment, eras are fixed periods of time (rather than rolling windows), and era and epoch goals are adjusted each era based on usage during the previous era. In this embodiment, at the end of an epoch within an era, operation 80 includes determining whether compliance by the subject has exceeded or fallen short of epoch and/or era goals to a degree that adjustment is warranted. For instance, if the subject reaches or exceeds an era goal corresponding to a week in just 5 or 6 nights, it may be determined at operation 80 that the era goal should be adjusted and/or a new era can be started or initialized. Similarly, if the usage of the subject has fallen well below the epoch goal on a nightly basis, and/or if the usage of the subject is well below the era goal for the current era, it may be determined at operation 80 that the epoch and/or era goals need to be adjusted to provide more realistic guidance to the subject. As another example, in one embodiment, an epoch goal is adjusted each epoch based on previous usage (e.g., during a current era that is a rolling window in time). In one embodiment, operation 80 is performed by a goal module that is the same as or similar to goal module 40 (shown in FIG. 1 and described above).

If it is determined at operation 80 that the usage goal(s) do not need to be adjusted, method 54 may proceed back to operation 70 using the current usage goal(s) to monitor further compliance. If it is determined at operation 80 that at least one of the usage goal(s) does need to be adjusted, method 54 proceeds back to operation 68 and the usage goal(s) are adjusted based on past usage. For example, at operation 68, the usage goal(s) may be adjusted based on past usage in the manner described above with respect to operation 68.

It will be appreciated that as time goes on method 54 is designed to slowly increment the usage goal(s) upward to encourage the subject to receive more and more positive airway pressure treatment. In one embodiment, the amount of treatment or therapy that method 54 encourages the subject to receive has an upper limit. This upper limit may correspond to the amount of actual sleep that the subject gets. For example, if the subject typically gets approximately 8 hours of sleep a night, the upper limit may be 7 hours of sleep a night (or some other amount of time less than or equal to 8 hours). This upper limit is configurable, and may be set by the subject and/or the caregiver via a user interface. In one embodiment, as the usage goal(s) are adjusted at operation 68 to values closer and closer to the upper limit, and the usage of the subject monitored at operation 74 gets closer and closer to the upper limit, operation 68 may increment the usage goal(s) upward at a slower rate.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to provide feedback to a subject regarding compliance to a positive airway pressure support therapy regime, the system comprising:
   a pressure support device configured to generate a pressurized flow of breathable gas for delivery to an airway of a subject;
   one or more sensors configured to generate output signals that indicate whether the pressurized flow of breathable gas is being received into the airway of the subject;
   one or more processors configured to implement computer program modules, the modules comprising:
      a usage module configured to monitor usage of the pressure support device by the subject, wherein usage of the pressure support device by the subject includes receiving the pressurized flow of breathable gas into the airway;
      a goal module configured to determine a usage goal, wherein the usage goal is based on past usage of the pressure support device by the subject, and wherein the usage goal indicates a duration of reception by the subject, of the pressurized flow of breathable gas;
      a compliance module configured to determine whether the usage of the pressure support device by the subject has met or exceeded the usage goal; and
      a feedback module configured to provide feedback to the subject that indicates to the subject information related to the usage of the pressure support device with respect to the usage goal.

2. The system of claim 1, wherein the feedback includes encouragement to the subject, wherein the encouragement is different than the information related to the usage of the pressure support device with respect to the usage goal.

3. The system of claim 1, wherein the usage module is configured to monitor the usage during multiple days, wherein the multiple days include a most recent day and a least recent day, and wherein the goal module is configured to determine the usage goal by aggregating the monitored usage during the multiple days by using a greater weighting factor for the most recent day than for the least recent day.

4. The system of claim 1, wherein the compliance module is further configured to prorate the usage goal for a particular day based on
   (a) the usage goal,
   (b) current time, and
   (c) monitored usage for an elapsed portion of the particular day, wherein the compliance module is further configured to determine, based on the prorated usage goal, whether the usage of the pressure support device by the subject during the elapsed portion of the particular day is on track to meet or exceed the usage goal for the particular day.

5. The system of claim 1, wherein the feedback module is further configured to generate feedback for a caregiver located remotely from the subject, and wherein the feedback generated for the caregiver indicates to the caregiver information related to the usage of the pressure support device with respect to the usage goal.

6. A method of providing feedback to a subject regarding compliance to a positive airway pressure support therapy regime, the method comprising:
   generating a pressurized flow of breathable gas for delivery to an airway of a subject;
   monitoring usage by the subject of the pressurized flow of breathable gas;
   determining a usage goal, wherein the usage goal is based on past usage of the pressurized flow of breathable gas by the subject, and wherein the usage goat indicates a duration of reception, by the subject, of the pressurized flow of breathable gas;
   determining whether the usage by the subject has met or exceeded the usage goal; and
   providing feedback to the subject that indicates to the subject information related to the usage of the pressurized flow of breathable gas with respect to the usage goal.

7. The method of claim 6, wherein providing feedback includes providing encouragement to the subject, wherein the encouragement is different than the information related to the usage of the pressurized flow of breathable gas with respect to the usage goal.

8. The method of claim 6, wherein monitoring the usage is performed during multiple days, wherein the multiple days include a most recent day and a least recent day, and wherein determining the usage goal includes aggregating the monitored usage during the multiple days by using a greater weighting factor for the most recent day than for the least recent day.

9. The method of claim 6, wherein determining whether the usage by the subject has met or exceeded the usage goal includes:
   prorating the usage goal for a particular day based on
      (a) the usage goal,
      (b) current time, and
      (c) monitored usage for an elapsed portion of the particular day; and
   determining, based on the prorated usage goal, whether the usage of the pressurized flow of breathable gas by the subject during the elapsed portion of the particular day is on track to meet or exceed the usage goal for the particular day.

10. The method of claim 6, further comprising generating feedback for a caregiver located remotely from the subject, wherein the feedback generated for the caregiver indicates to the caregiver information related to the usage of the pressure support device with respect to the usage goal.

11. A system configured to provide feedback to a subject regarding compliance to a positive airway pressure support therapy regime, the system comprising:
   means for generating a pressurized flow of breathable gas for delivery to an airway of a subject;
   means for monitoring usage by the subject of the pressurized flow of breathable gas at the airway of the subject;
   means for determining a usage goal, wherein the usage goal is based on past usage of the pressurized flow of breathable gas by the subject, and wherein the usage goal indicates a duration of reception, by the subject, of the pressurized flow of breathable gas;
   means for determining whether the usage by the subject has met or exceeded the usage goal; and
   means for providing feedback to the subject that indicates to the subject information related to the usage of the pressurized flow of breathable gas with respect to the usage goal.

12. The system of claim 11, wherein the means for providing: feedback is further configured to provide encouragement to the subject, wherein the encouragement is different than the information related to the usage of the pressurized flow of breathable gas with respect to the usage goal.

13. The system of claim 11, wherein the means for monitoring: the usage is configured to monitor the usage for multiple days, wherein the multiple days include a most recent day and a least recent day, and wherein the means for determining the usage goal is configured to aggregate the monitored usage during the multiple days by using a greater weighting factor for the most recent day than for the least recent day.

14. The system of claim 11, wherein the means for determining whether the usage by the subject has met or exceeded the usage goal is further configured to:
   prorate the usage goal for a particular day based on:
      (a) the usage goal,
      (b) current time, and
      (c) monitored usage for an elapsed portion of the particular day and
   determine, based on the prorated usage goal, whether the usage of the pressurized flow of breathable gas by the subject during the elapsed portion of the particular day is on track to meet or exceed the usage goal for the particular day.

15. The system of claim 11, further comprising means for generating feedback for a caregiver located remotely from the subject, wherein the feedback generated for the caregiver indicates to the caregiver information related to the usage of the pressure support device with respect to the usage goal.

* * * * *